United States Patent [19]

Törnblom et al.

[11] 4,237,419
[45] Dec. 2, 1980

[54] METHOD AND APPARATUS FOR NON-DESTRUCTIVE TESTING USING A PLURALITY OF FREQUENCIES

[75] Inventors: Bengt H. Törnblom; Torborg M. Törnblom, both of Västerås, Sweden

[73] Assignee: Tornbloms Kvalitetskontroll AB, Västeras, Sweden

[21] Appl. No.: 913,313

[22] Filed: Jun. 7, 1978

[51] Int. Cl.³ ............... G01N 27/82; G01R 33/12
[52] U.S. Cl. ............................ 324/225; 324/227; 324/232; 324/237
[58] Field of Search ............ 324/225, 226, 228, 232, 324/233, 234, 237, 238

[56] References Cited

U.S. PATENT DOCUMENTS

| 3,229,198 | 1/1966 | Libby | 324/233 |
| 3,706,029 | 12/1972 | Wandling et al. | 324/227 |
| 3,974,442 | 8/1976 | Savidge et al. | 324/225 |

FOREIGN PATENT DOCUMENTS 1095625 12/1967 United Kingdom ............ 324/232

Primary Examiner—Gerard R. Strecker
Assistant Examiner—Walter E. Snow
Attorney, Agent, or Firm—Lewis H. Eslinger

[57] ABSTRACT

A method and device for nondestructive testing of articles using the eddy principle current and multifrequency technique. The characteristic feature is that the measurement is generally independent of the position of the article to be tested in relation to the pickup probe. In comparison with known devices the present device is easy to handle.

24 Claims, 8 Drawing Figures

METHOD AND APPARATUS FOR NON-DESTRUCTIVE TESTING USING A PLURALITY OF FREQUENCIES

BACKGROUND OF THE INVENTION

The present invention relates to a method and device for testing conductive articles such as bodies, metal sheets, blanks, wires, tubes liquids, powders etc. with respect to changes such as errors, defects, deviations, dimensional changes, changes in the electrical properties, including changes caused by external influence, such as speed, force etc. The method and device according to the invention provides for detection and evaluation of the change, for example its type, size, position etc. A detectec change, for example originating from dimensional changes, is adapted to be measured thereby providing a measure of the dimension and the dimensional change respectively. If the change originates from mechanical stresses in the test specimen, for example from external force applied to the test specimen, the stress is measured and a measure of the force and change of force is obtained. If said change originates partly or completely from relative motion between the test specimen and the pickup probe a measure of the speed of the test specimen passing said probe is obtained. Integrating said speed will provide a measure of the length of the specimen which has passed the probe. The change or error may also originate from a change from presence of material to non-presence of material in which case the device is suitable as metal detector.

Devices for performing nondestructive testing are previously known and include at least one pickup probe excited by alternating current. The magnetic field of the coil generates eddy currents in the test specimen and changes in the test specimen appear in the form of changes in the distribution of the eddy currents. The eddy currents are detected by pickup probes which in the known devices often form a part of a balanced bridge circuit or other similar unbalance circuits.

Said known devices are often of the self comparison type, that is, a section the specimen constitutes a reference or normal for another section thereof which implies that such devices are not suitable for the detection of so called oblong defects such as long cracks etc.

It is also previously known to make use of devices wherein the pickup probe is excited with multiple frequencies, compare for instance the method of H. L. Libby described in Introduction to Electromagnetic Nondestructive Test Methods/Whiley o Sons, Inc. 1971. Said method is based upon Fourier transformation.

In these known devices it is difficult if not impossible to separate, in a simple and practical way, the so called error signal, that is the signal originating or emanating from a change, from position signals originating from the position of the pickup probe in relation to the test specimen. This implies that these devices do not operate satisfactory when the test specimen for example is vibrating. However, in most practical applications the test specimen is vibrating which, when so called through pickup probes are used, implies that the movement of the test specimen in relation to the radial extent of the pickup probe will give rise to a position signal modulated by said movement, said modulated signal often dominating over the error signal emanating or originating from said defect. When using so called surface pickup probes a modulation caused by the position variation between pickup probe and test surface is obtained in a corresponding manner.

In the Swedish printed and published Swedish Pat. No. 75.07857-6 there is disclosed a device which provides for detection of changes of an article independent of the position of the pickup probe in relation to the test specimen. The device described therein comprises like the present invention, at least one pickup probe or at least one wire loop which is excited with at least two different frequencies. Like the present invention the device is calibrated against for example a reference specimen. This calibration takes place at a certain distance between the reference specimen and the pickup probe. The calibrated device is then used for testing. When the pickup probe is at a certain distance (point $P_{min}$ in FIG. 4) which is depending on the change, from the test specimen the change cannot be detected. This is of course a drawback. The present invention is directed to solve this problem and other problems related thereto.

BRIEF DESCRIPTION OF THE DRAWINGS

The invention will now be described in connection with the accompanying drawings wherein.

DETAILED DESCRIPTIONS OF PREFERRED EMBODIMENTS

Figure 1:
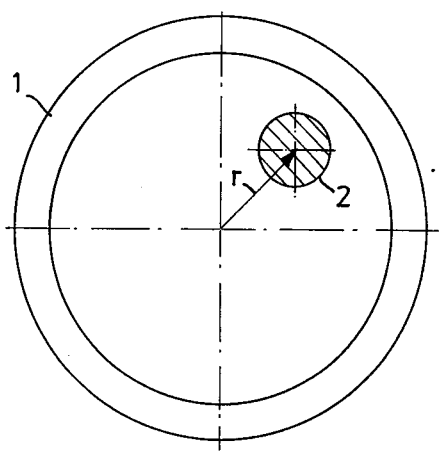
FIG. 1 is a cross section view of a pickup probe surrounding the article to be tested.

In FIG. 1 there is shown a through pickup probe 1 surrounding the article 2 to be tested. Said article 2, also referred to as the test specimen, is positioned eccentric and at a distance r from the center axis of the pickup probe. The article may for example be a continuous length of rod wire. The pickup probe is excited from at least one generator which generates output signals of at least two different frequencies. The output signals from said generator may be sinusoidal or may be in the form of pulses or pulse trains. The output signals may have a variable amplitude and mutually fixed or variable phase angles. Moreover, the output signals of said generator may be frequency modulated, eventually in accordance with a suitable time function.

Figure 2:
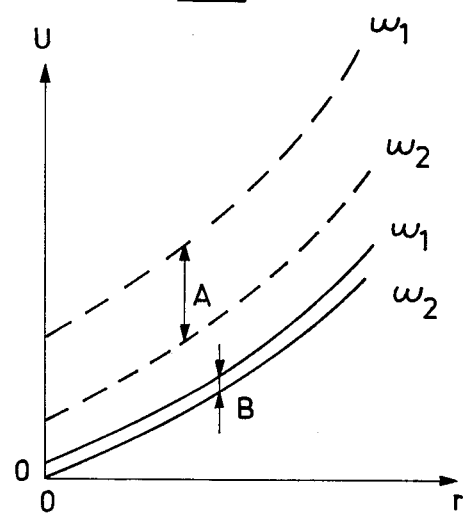
FIG. 2 is a diagram showing an example of a so called pickup probe variable as a function of the position of said probe in relation to the tested article, said variable being measured at two different frequencies, as well as the same pickup probe variable measured in relation to a reference specimen at both frequencies.

In FIG. 2 there is shown a pickup probe variable, in this particular case a voltage U, as a function of the position or center distance r of said article measured at two different frequencies $w_1$ and $w_2$ respectively. The voltage amplitudes are shown on the one hand for a test specimen exhibiting a change, in the drawing and below referred to as error, and on the other hand for a specimen without any change, in the drawing and below referred to as error (not error).

As appears from FIG. 2 the absolute value $|A|$, which inter alia is a function of a change such as the error or defect in the test specimen, is greater than the absolute value $|B|$ for all useful values of r. This is used for error or defect detection in accordance with said Swedish patent specification.

In order to simplify the signal treatment the pickup probe variable has been compensated so, that minimum for each of the frequencies will be at one and the same value of r, preferably $r=0$ when testing a specimen without any changes. Such compensation may include what is referred to as balancing or zero compensation. Such zero compensation may preferably be achieved with the aid of a servo mechanism.

Depending on the actual type of change the optimum electrical quantity and suitable frequencies $w_1$ and $w_2$ are selected to obtain optimum test results. The expression electrical quantity as used herein refers to direct variables such as resistance, inductance etc. as well as indirect variables such as voltage, current magnitude, phase etc. all such variables including any possible influence (interaction) from the test specimen via the electrical coupling between test specimen and pickup probe. The electrical quantities are influenced in varying degrees at different frequencies when there is a change in the test specimen.

Figure 3:
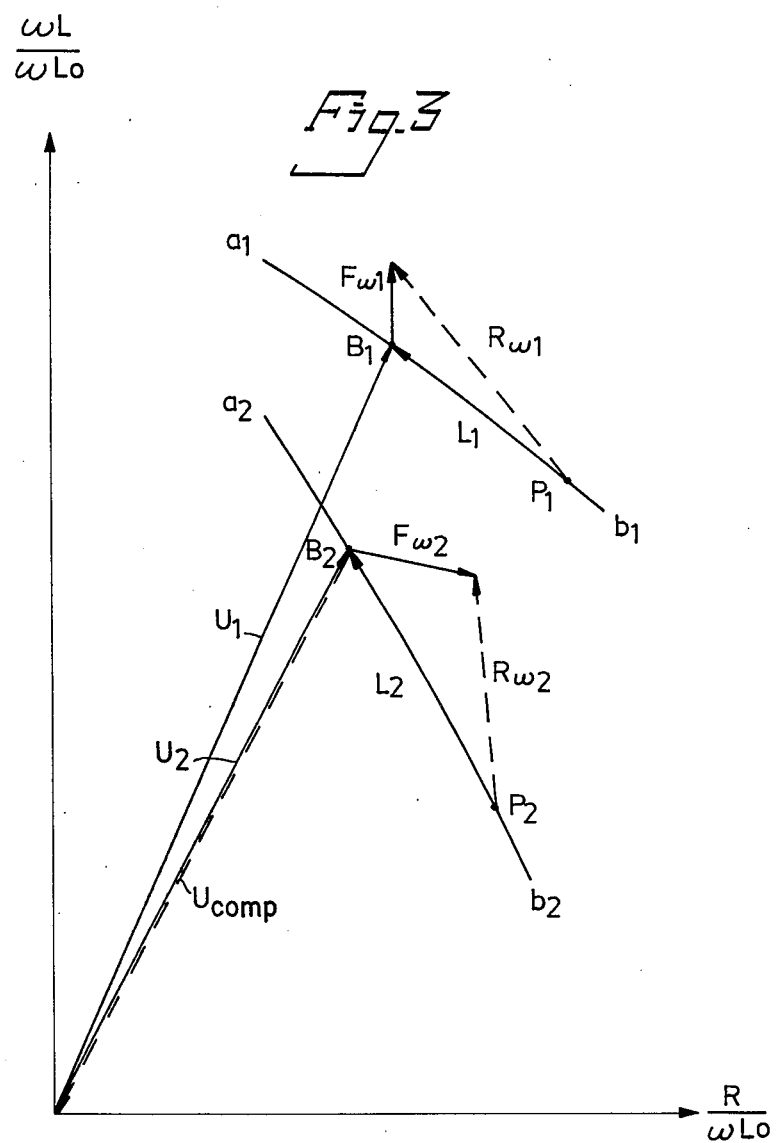
FIG. 3 is a complex impedance diagram or rather portions thereof for the pickup probe shown in FIG. 1.

The electrical properties of a pickup probe are preferably described with the aid of a so called complex, often normalized, impedance diagram. In FIG. 3 portions of a simplified impedance diagram are shown for a specific pickup probe. In the axis definitions R is the resistance of the pickup probe, $wL_o$ is the impedance of said probe without any test specimen inserted and wL is the impedance of the probe with a test specimen inserted.

For the sake of simplicity the following discussion is restricted to the use of two different frequencies $w_1$ and $w_2$ although the discussion is valid also for multiple frequencies.

Figure 4:
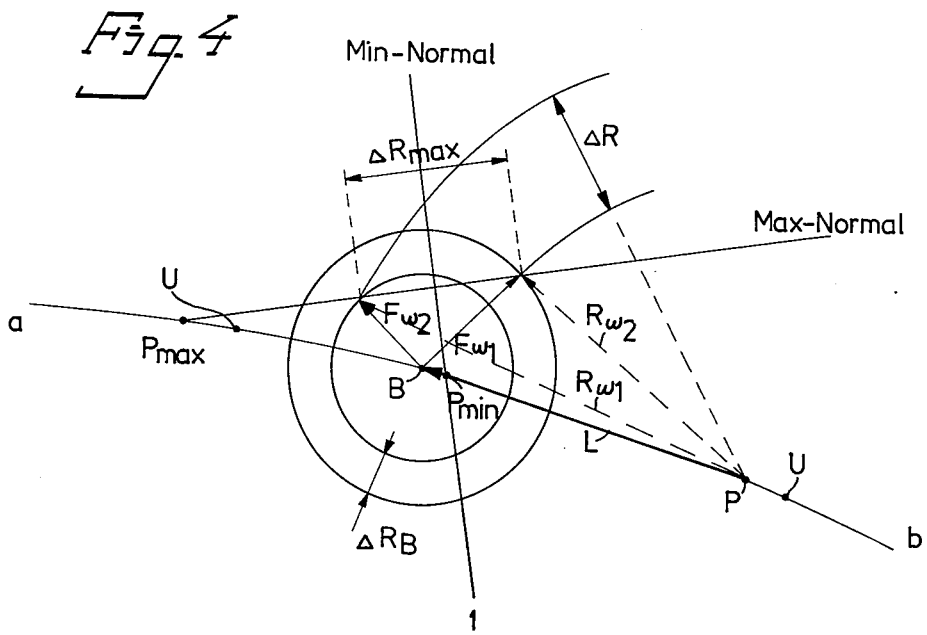
FIG. 4 is a simplified complex impedance diagram illustrating the method in accordance with the present invention when using amplitude detectors; said method providing for the detection of changes or errors in or at said article with maximum sensitivity independent of the direction and size of the change.

When the position of the pickup probe is varied in relation to the test specimen the impedance of the probe at the frequency $w_1$ is altered along the line $a_1$ to $b_1$, that is it will alter in a certain direction (called the lift-off direction in case a so-called surface pickup probe is used) and in a similar manner the impedance of the pickup probe is altered along the line $a_2$ and $b_2$ for the frequency $w_2$. The described change of position corresponds to a position signal (or rather a position vector) for each of the frequencies. In FIG. 3 said position changes are represented by the position signals $L_1$ and $L_2$ at each frequency $w_1$ and $w_2$. If the test specimen has a change, for example a defect, said change will give rise to impedance changes in the pickup probe. Said impedance changes will appear in the complex impedance diagram. Depending on the source of the change such impedance changes will have different sizes and directions for different frequencies. In FIG. 4 said impedance changes originating from changes or errors in said specimen are represented by error signals (rather error vectors) $F_{w1}$ and $F_{w2}$ for each respective frequency $w_1$ and $w_2$. Vectors $U_1$ and $U_2$ represent the impedance of or (the voltage across) said pickup probe when there is no change in the specimen. In practice the probe is excited with current having multiple frequencies, such as for example $w_1$ and $w_2$. There will then be a voltage drop across the probe, said voltage drop being represented by the said vectors $U_1$ and $U_2$, the absolute value and phase of which are directly depending on the impedance of the pickup probe. In the following discussion it is suposed that the pickup probe is excited with current comprising the frequencies $w_1$ and $w_2$. If the probe is placed over an article without any change, that is an article which may serve as a reference or normal, then it is easy to compensate (zero compensate) away the voltage over the probe in this particular position of the probe, said position being referred to as the compensation point, by introducing oppositly directed compensation voltages (or rather compensation vectors) of which only compensation vector $U_{comp}$ for the voltage drop $U_2$ is shown with the dotted line in FIG. 3. In principle, it makes no difference which type of electrical quantity, that is pickup probe variable or combination of such variables, that is used or measured. Suppose that the compensation is performed in the points correspond to points $B_1$ and $B_2$ in FIG. 3, that is $B_1$ and $B_2$ relate to one and the same position of the pickup probe in relation to the test specimen. When said compensation has been performed deviations or changes in the relative position probe-specimen will directly, or indirectly via compensating circuits, appear as electrical signals (vectors), for example voltage vectors, originating from the pickup probe.

With the expression of compensation circuits as used herein analogue as well as digital compensation arrangements including programmed electronic equipment such as computers etc. are contemplated. Such electrical signals (vectors) which originate from changes or deviations in relation to the compensation point are often referred to as unbalance, for example position unbalance, error unbalance, dimensional unbalance etc.

In accordance with the present invention vectors $L_1$ and $L_2$ are now made equivalent from measuring point of view which in the following will be referred to as normalization.

To carry out the normalization the following procedure may be used; the excitation current of the pickup probe for each frequency $w_1$ and $w_2$ is given such a value that $|L_1|$ and $|L_2|$ are made equivalent. This can be performed directly or indirectly in signal treating circuits. By selecting a suitable form of the pickup probe and by selecting suitable frequencies this equivalency between the position vectors (that is the position signals) $L_1$ and $L_2$ may be maintained over a relatively wide interval $a_1-b_1$.

It is now supposed that the detectors by which the normalized position signals are detected are not phase sensitive but amplitude sensitive. Thanks to the normalization line segements $a_1-b_1$ and $a_2-b_2$ in FIG. 3 may be transformed into one single position signal (position vector) L as has been done in FIG. 4.

As long as there are no error signals (error vectors) originating from a change, which error signals have been labeled $F_{w1}$ and $F_{w2}$ in FIGS. 3 and 4, the difference between $|L_1|$ and $|L_2|$ will, thanks to the normalization, remain constant, for example 0, independent of the position, that is position P in FIG. 4, of the pickup probe in the relation to the test specimen. Now, the error signals $F_{w1}$ and $F_{w2}$ originating from a change and shown in FIG. 3 are added to the normalized position vector L. As a result of this addition resulting vectors $R_{w1}$ and $R_{w2}$ are achieved. The difference between $|R_{w1}|$ and $|R_{w2}|$ is not zero (except in one point, namely when point P coincides with point $P_{min}$) and this fact is used to detect changes in the specimen independent of the position of the pickup probe in relation to the test specimen.

However, it may happen that the above mentioned compensation point due to practical reasons will move along line a-b towards point B, that is in a certain point $P_{min}$ the absolute value $|R_{w1}|$ will be equal to $|R_{w2}|$ and the difference $\Delta R$ of the resulting vectors $R_{w1}$ and $R_{w2}$ will be zero. This means that in said point $P_{min}$ any change in the test specimen cannot be detected. The present invention is concerned with the solution to this problem and other problems related thereto. In theory this problem can be solved by physically varying the mutual position pickup probe-test specimen. An equivalent to this is to electrically simulate the position variation of the pickup probe relative to the test specimen, in other words to perform an apparent movement along curve section a-b in FIG. 4. This can be accomplished by performing compensation at least at two different positions between pickup probe and test specimen. Said positions are represented by two different points $COMP_I$ and $COMP_{II}$ along curve section a-b in FIG. 4. The first compensation (which will provide voltage $U_{comp\,I}$) will then eliminate vectors $U_1$ and $U_2$ (shown in FIG. 3) while the other (which will provide voltage $U_{comp\,II}$) only will eliminate the impedance variation caused by the different positions of compensation points. Now, by varying the $U_{comp\,II}$ (compare FIG. 5) an "apparent" movement along curve a-b is achieved. During this apparent movement in the complex impedance plane along curve a-b the difference $\Delta R = |R_{w1}|$ minus $|R_{w2}|$ will, if there is a change in the test specimen, appear with a reinforced or amplified effect when point P "moves" closer to point $P_{max}$. At point $P_{max}$ said difference $\Delta R$ is at maximum and its absolute value is $\Delta R_{max}$ which has been indicated in FIG. 4. At point B said difference is $\Delta R_B$. This variation of the compensation variable may be rhytmic and may have a pace or rate which often is slower than $w_1$ and $w_2$. To summarize $\Delta R$ will be greater when point P is within a specific interval (near $P_{max}$) of line a-b than within other intervals ($P_{min}$). This is used to provide a safe and powerful detection of changes in or at the test specimen. If said variation is performed at a certain frequency, or in accordance with any other selected function, $\Delta R$ will appear as a signal "modulated" with said frequency or with said function. The "degree of modulation" will then contain information concerning the change. Accordingly the change is detected with optimum sensitivity independent of the relative position pickup probe-test specimen and/or the phase angle of said change (that is the phase angle of the error vector in relation to any selected reference direction).

Figure 7A:
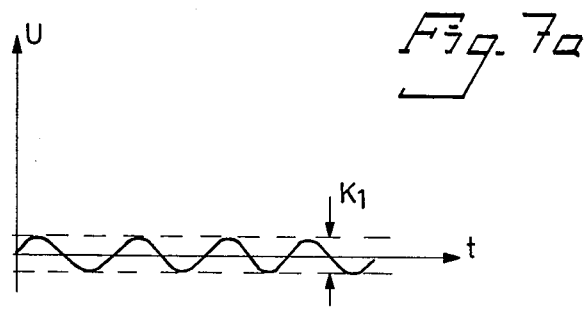
FIG. 7a is a voltage diagram showing the difference signal as formed in accordance with the present invention when there is no change in or at the tested article.
Figure 7B:
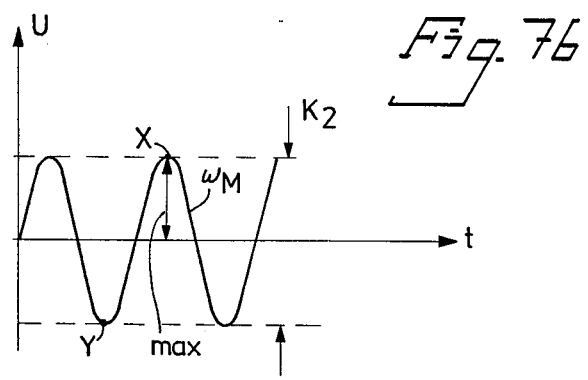
FIG. 7b is a voltage diagram similar to that of FIG. 7a but for an article which has a change.

The above mentioned normalization which is a characteristic feature of the present invention imples that $L \sim L_1 \sim L_2$ (comp. FIGS. 3 and 4) independent of the absolute value of L. In other words, if the test specimen has no change then the above-mentioned variation of L will not give rise to any $\Delta R$ or any variation of $\Delta R$. Examples of this are shown in FIGS. 7a and 7b. Often a weighting procedure is used in order to have $L_1 = L_2$ which means that $L_1$ and $L_2$ need not be two identical quantities (values) in order to be equivalent from the measuring point of view.

The term weighting as used herein will now be discussed with reference to FIG. 2 in which one of the variables of the pickup probe is shown as a function of the position of the test specimen relative to the pickup probe, said variable being measured at two different frequencies $w_1$ and $w_2$. If the probe variable is written $G = (w,r)$ the following relations are valid when there is no change in the test specimen; if the ratio between $G_{w1}$ and $G_{w2}$ is different from 1, that is $G_{w1}/G_{w2} = k$ and $k = $ constant $\neq 1$ then $G_{w1} = k \cdot G_{w2}$ and $G_{w2}$ is said to be weighted for example in said compensation circuits, with k in order to be equivalent with $G_{w1}$ thereby providing a constant difference between $G_{w1}$ and the new value of $G_{w2}$, said new value being $k \cdot G_{w2}$. This means that the invention also includes the case when the ratio between $G_{w1}$ and $G_{w2}$ is constant and is different from 1.

If the difference (B) between $G_{w1}$ and $G_{w2}$ in certain points is not constant although weighting has been performed then this deviation may be eliminated by so called linearization. The term linearization as used herein means that $G_{w1}$ and/or $G_{w2}$, for example by way of function generation, is converted so that the said difference (B) will remain constant.

To summarize, this means that the present invention in principle may be used for any selected pickup probe variable functions. This is a feature that not can be found in the apparatuses belonging to the state of the art.

Figure 5:
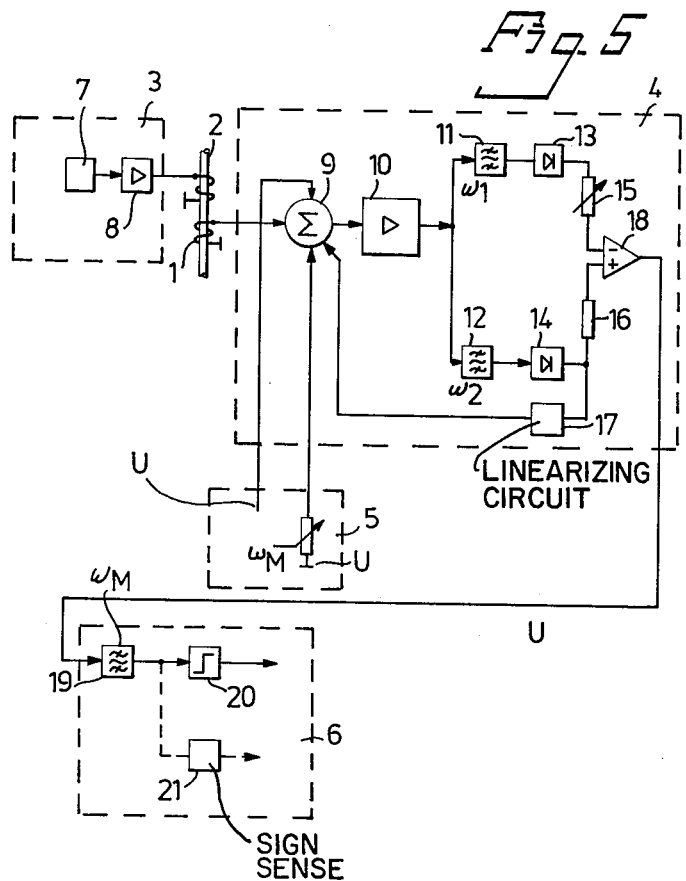
FIG. 5 is a block diagram showing an illustrative embodiment of the device in accordance with the present invention when using amplitude modulated rectifiers.

FIG. 5 is a block diagram of a first embodiment of an apparatus for carrying out the method in accordance with the present invention. Besides the pickup probe 1 and the test specimen 2 the apparatus comprises four main blocks, namely block 3 representing circuits which are used for excitation of the pickup probe, block 4 representing circuits which are used for detection and treatment of the previously mentioned electrical quantities, block 5 representing circuits by which the compensation voltage is varied and block 6 representing circuits which are used to treat the error signal information received from block 4. An oscillator 7 delivers currents comprising at least frequencies $w_1$ and $w_2$. The currents are amplified in an amplifier 8 and are fed to a primary winding of the probe. A second winding on the probe is connected to a first input of a summation amplifier 9 which at a second and third input is supplied with the compensation voltages $U_{comp\,I}$ and $U_{comp\,II}$ respectively, said voltage $U_{comp\,I}$ being oppositely directed to vectors $U_1$ and $U_2$ in FIG. 3 and voltage $U_{comp\,II}$ being directed along vector L in FIG. 4. One of the compensation voltages, for example $U_{comp\,II}$ is varied (modulated) with a frequency $w_M$ which for example may be ten times slower than the frequencies of the current from said oscillator 7. The output of summation amplifier 9 is connected to a power amplifier 10 the output of which is connected on the one hand to a filter 11 adapted to one of said frequencies, for example $w_1$, and on the other hand to a second filter 12 adapted to the other of said frequencies, that is $w_2$. The output from filter 11 is rectified in an amplitude rectifier 13 and in a corresponding manner the output signal from filter 12 is rectified in another amplitude rectifier 14. The output signal from rectifier 13 is, via a potentiometer 15, connected to one input of a differential amplifier and the output of rectifier 14 is, via a resistor 16, connected to the other input of said differential amplifier. A part of the output signal from rectifier 14 is fed back via a linearizing circuit 17 to a fourth input of summation amplifier 9. Potentiometer 15 performs the above described normalization of the position signals. The output from said differential amplifier 18 is applied to a filter 19 which is adapted to the previously mentioned variation frequency $w_M$. The output signal from filter 19 is applied to a level switch 20 which delivers an output signal when the output signal from filter 19 exceeds a certain level (referred to as $k_1$ in FIG. 7a) and simultanously equals or is smaller than another, higher level (referred to as $k_2$ in FIG. 7b) thereby indicating that an error or change is present in the test specimen. A sign sensing circuit 21 may be connected to the output of filter 19 for purposes described further down.

Figure 6:
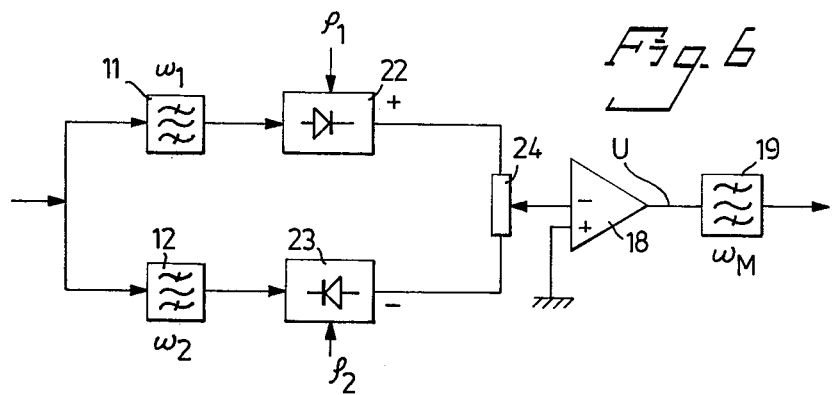
FIG. 6 is a block diagram showing a modified version of the device in accordance with FIG. 5, the difference being that the detectors are phase controlled rectifiers, so called synchronous demodulators or controlled rectifiers.

In FIG. 6 a modified version of the circuit of FIG. 5 is shown. Instead of the pure amplitude rectifiers 13, 14 in FIG. 5 two phase controlled rectifiers 22 and 23 are used. Instead of the compensation voltage $U_{comp\ II}$ a steady or unmodulated compensation voltage is used. Rectifiers 22, 23 are controlled each by a separate control phase $\alpha_1$ and $\alpha_2$ which are mutually phase synchronized. The output signals from the phase controlled rectifiers are applied at opposite ends of a potentiometer 24 the sliding contact of which is connected to one input of said differential amplifier 18. The other input of said amplifier is connected to earth or another suitable reference voltage. Also in this embodiment potentiometer 24 serves as a normalizing circuit. Following the differential amplifier 18 the signal treatment is the same as in FIG. 5. Control phases $\alpha_1$ and $\alpha_2$ are varied with an equal number of electrical degrees per time unit and the control signals are in a fixed mutual relation to each other.

The described device is an example of how phase controlled detectors, the control phase of which are varied (for example by varying $L_1$ and $L_2$), may be used to detect the difference and/or the ratio between for example the error vectors at different frequencies without knowing in advance the phase positions of said vectors.

Amplitude detectors 13 and 14 of FIG. 5 can be considered as controlled detectors the control signal of which are $U_{comp\ I}$ and $U_{comp\ II}$, control voltage $U_{comp\ II}$ being varied. In other words there is a direct analogy between the circuits of FIG. 5 and 6.

FIG. 7a is a diagram showing, for the electrical quantity of the pickup probe, that the difference between two corresponding electrical signals, each at different frequencies (such as $w_1$ and $w_2$), may be a constant $=k_1$ if there is no change in the test specimen, while FIG. 7b is showing the corresponding difference signal when there is a change in the test specimen. This signal may also be constant $=k_2$ and may have the above-mentioned variation $w_M$. The control signals to the detectors may preferably be locked in an optimum position with regard to the actual test performed so that the change will be detected with the best possible sensitivity. In FIG. 7b it is preferred to lock the control signal at points x and y where $U_{diff}$ is at maximum. These points correspond to the points where the derivative of $U_{diff}$ is shifting its sign. In FIG. 5 the sign sensing circuit 21. is sensing this sign shifting and is used to lock the control signals in said preferred positions. After the device has been locked in the optimum position with regard to the change to be detected the change is detected and evaluated, for example with regard to the source of the change.

The invention has been described in connection with only one pickup probe. Of course, several pickup probes may be arranged in series and said probes may then be connected to one common signal generator. If the electrical quantities from each probe are delayed so that a resulting combined signal is achieved excellent noise supression is achieved, particularly when there is a relative movement between test specimen and pickup probe.

The invention has been described in connection with only two frequencies. However, multiple frequencies may be used as well and this will provide more information concerning the change implying that the properties of the change, such as its form orientation, size etc., may be evaluated with a high degree of accuracy. In practice it is convenient to mark a detected change with paint to make it easy to recover the position of said change in or at the specimen.

The above described embodiments of the invention may be varied and modified within the scope of the present invention.

What is claimed is:

1. A method of testing a conductive article using a test probe having a variable physical relationship to said article comprising:
    applying an alternating magnetic field having at least first and second different frequencies to said article from said test probe;
    sensing at least one electrical quantity responsive to said variable physical relationship having first and second components responsive to said first and second different frequencies respectively;
    cyclically electrically adding a third component to said first component to produce a fifth component and cyclically electrically adding a fourth component to said second component to produce a sixth component, said fifth and sixth components being effective to cyclically electrically simulate a change in a physical relationship related to said variable physical relationship whereby testing results are obtained regardless of said variable physical relationship;
    detecting said fifth and sixth components to produce first and second detected components;
    subtracting one of said first and second detected components from the other thereof to produce an output signal; and said output signal containing information about a change in said article 2. A method according to claim 1, further comprising substracting an inverse of said first and second components from said first and second components respectively corresponding to a particular physical relationship of said test probe and said article sufficient to reduce said first and second components to the same predetermined value.

3. A method according to claim 2, further comprising weighting one of said first and second components to make it equal to the other thereof.

4. A method according to claim 1, further comprising weighting one of said first and second components to make it equal to the other thereof.

5. A method according to claim 1, further comprising linearizing at least one of said first and second components whereby a difference therebetween remains constant over a substantial range of variation of said variable physical relationship.

6. A method according to claim 1, wherein the step of cyclically electrically adding said third and fourth components includes cyclically electrically varying at a third frequency and further includes a step of sensing a magnitude of cyclic variation including the step of passing said output signal through a filter which is responsive to said third frequency.

7. A method according to claim 1, further comprising:
sensing when a cyclic variation in said output signal attains a maximum; and
locking said third and fourth components at values which produce said maximum.

8. A method according to claim 1, wherein said output signal indicates a characteristic of a dimension of said article.

9. A method according to claim 1, wherein said output signal indicates a characteristic of a force applied to said article.

10. A method according to claim 1, wherein said output signal indicates a characteristic of a speed of said article.

11. A method according to claim 1, wherein said output signal indicates a dimension of said article.

12. A method according to claim 1, wherein said physical relationship is a distance and said method further comprises holding said distance constant.

13. A method according to claim 1, further comprising
subtracting an inverse of said first and second components from said first and second components respectively corresponding to a particular physical relationship of said test probe and said article sufficient to reduce said first and second components to the same predetermined value;
weighting one of said first and second components to make it equal to the other thereof;
said first and second components each being reduced to zero at a first condition of said physical relationship by said step of subtracting an inverse therefrom; and
said step of cyclically electrically adding third and fourth components to said first and second components being effective at at least one value of said third and fourth components to reduce said fifth and sixth components to zero at a second different condition of said physical relationship.

14. A method according to claim 13, wherein said first, second, third, fourth, fifth and sixth components are complex variables defineable in a complex impedance plane.

15. A method according to claim 1, wherein said output signal indicates the presence and absence of said article.

16. Apparatus including at least one test probe for testing a conductive article having a variable physical relationship to said article comprising:
means for exciting said pickup probe with at least first and second frequencies;
means for sensing at least one electrical quantity responsive to said means for exciting, said at least one quantity having at least a first component responsive to said first frequency and a second component responsive to a second frequency;
means for zero compensating said first and second components at at least one value of said variable physical relationship;
means for separating said first and second components;
means for detecting said first and second components to produce first and second detected components;
means for applying at least one control signal to said means for detecting;
said means for applying said at least one control signal including means for cyclically varying said at least one control signal in a manner which cyclically simulates a change in a physical relationship related to said variable physical relationship whereby testing results are obtained regardless of said variable physical relationship;
means for subtracting one of said detected components from the other thereof to produce an output signal; and
said output signal containing information about a change in said article.

17. An apparatus according to claim 16, further comprising normalizing means for making a characteristic of said first and second detected components equal to each other.

18. An apparatus according to claim 17, wherein said characteristic is an amplitude.

19. An apparatus according to claim 16, further comprising linearizing means for maintaining a difference between said first and second detected components equal over a substantial range of said physical relationship.

20. An apparatus according to claim 16, wherein said means for detecting includes first and second amplitude detectors receiving said first and second components, and said at least one control signal includes a variable control voltage.

21. An apparatus according to claim 20, wherein said variable control voltage is a periodic voltage having a period at least a multiple lower than the lowest of said at least first and second frequencies.

22. An apparatus according to claim 16, wherein said means for detecting includes first and second phase controlled rectifiers, said means for applying said at least one control signal includes means for applying a first cyclically varying control signal to said first phase controlled rectifier, means for applying a second cyclically varying control signal to said second phase controlled rectifier, a phase of said first and second cyclically varying control signals being synchronized.

23. An apparatus according to claim 27, wherein said phase is varied.

24. An apparatus according to claim 16, further comprising:
said control signal including a third frequency;
filter means responsive to said third frequency for filtering said output signal.

* * * * *